US00PP19503P3

(12) United States Plant Patent
Lyrene

(10) Patent No.: US PP19,503 P3
(45) Date of Patent: Nov. 25, 2008

(54) 'SNOWCHASER'SOUTHERN HIGHBUSH BLUEBERRY

(50) Latin Name: ***Vaccinium corymbosum* L.**
Varietal Denomination: Snowchaser

(75) Inventor: Paul M Lyrene, Gainesville, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 535 days.

(21) Appl. No.: 11/288,766

(22) Filed: Nov. 30, 2005

(65) Prior Publication Data

US 2008/0196128 P1 Aug. 14, 2008

(51) Int. Cl.
*A01H 5/00* (2006.01)

(52) U.S. Cl. ..... Plt./157

(58) Field of Classification Search ..... Plt./157
See application file for complete search history.

*Primary Examiner*—Annette H Para
(74) *Attorney, Agent, or Firm*—Jondle & Associates, P.C.

(57) ABSTRACT

A new and distinct low-chill southern highbush (*Vaccinium corymbosum*) cultivar. Its novelty lies in the following unique combination of features:

1. Has a very low chilling requirement.
2. Has a vigorous bush with a somewhat spreading growth habit.
3. Ripens its berries between April 1 and April 30 in northest Florida.
4. Produces firm berries with a light-blue color and a good picking scar.

4 Drawing Sheets

Latin name of the genus and species. *Vaccinium corymbosum* L.
Variety denomination. 'Snowchaser'.

BACKGROUND OF THE INVENTION

The invention relates to a new and distinct variety of southern highbush blueberry (*Vaccinium corymbosum*L) hybrid named 'Snowchaser.' 'Snowchaser' is a southern highbush blueberry clone that is distinguished by its low chilling requirement and by its ability to produce medium-size, firm berries starting in early April and finishing before May 1 when grown in north Florida. Several hundred plants of 'Snowchaser' have been propagated by softwood cuttings at Gainesville, Florida, and the resulting plants have all been phenotypically indistinguishable from the original plant. Contrast is made to 'Star' (U.S. Plant Pat. No. 10675), an important variety widely planted in Florida and Georgia for early-season blueberry production. The new variety is important because it ripens much earlier than Star.

BRIEF SUMMARY OF THE INVENTION

'Snowchaser', when grown in north Florida, is distinguished from all other blueberry plants by the following combination of characteristics: has excellent vigor and very early leafing; ripens 18 days earlier than 'Star'; produces berries of medium size with good picking scar and firmness.

ORIGIN OF THE VARIETY

'Snowchaser' originated as a seedling from the cross FL95-57 (unpatented)×FL89-119 (unpatented) made as part of the University of Florida breeding program in a greenhouse in March, 1995. The seedling was first fruited in a high-density field nursery in the spring of 1997. After the second fruiting, which was observed in the field in the spring of 1998, 'Snowchaser' was propagated by softwood cuttings in June, 1998, and a 20-plant plot was established in a test plot in a commercial field at Windsor, Fla. in January 1999. Based on the very early ripening and good fruit quality from this plot, the plant was again propagated by cuttings, and 57 plants were planted in a second test plot at the same farm in March 2002. Several hundred additional plants were established at a test site in Archer, Fla. in January 2003.

BRIEF DESCRIPTION OF THE DRAWING

The color chart used in this specification is "The Pantone Book of Color", by Leatrice Eiseman and Lawrence Herbert. 1990. Harry N. Abrams, Inc., Publishers, N.Y. Where colors in the drawings differ from the Pantone color designations in the verbal descriptions, the Pantone color designations are the more accurate.

DETAILED BOTANICAL DESCRIPTION

Figure 1:
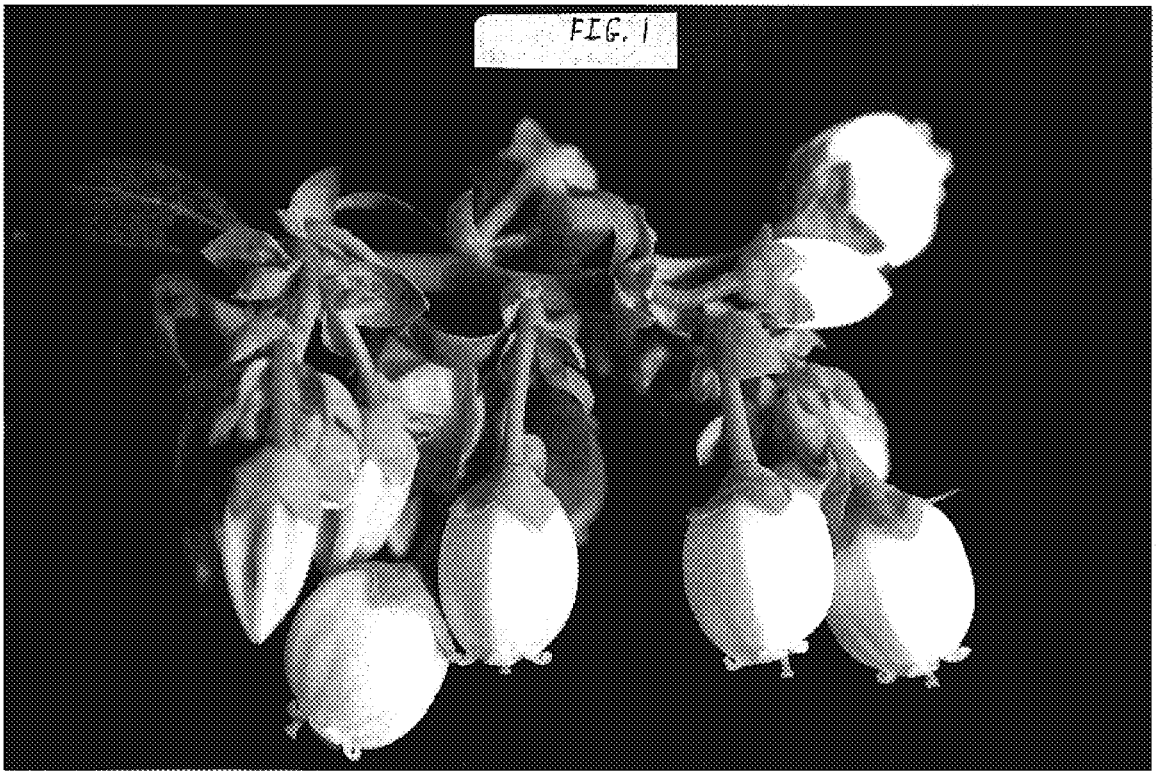
FIG. 1 shows flower clusters of 'Snowchaser' with the end of the styles extending beyond the tip of the corolla tubes.
Figure 2:
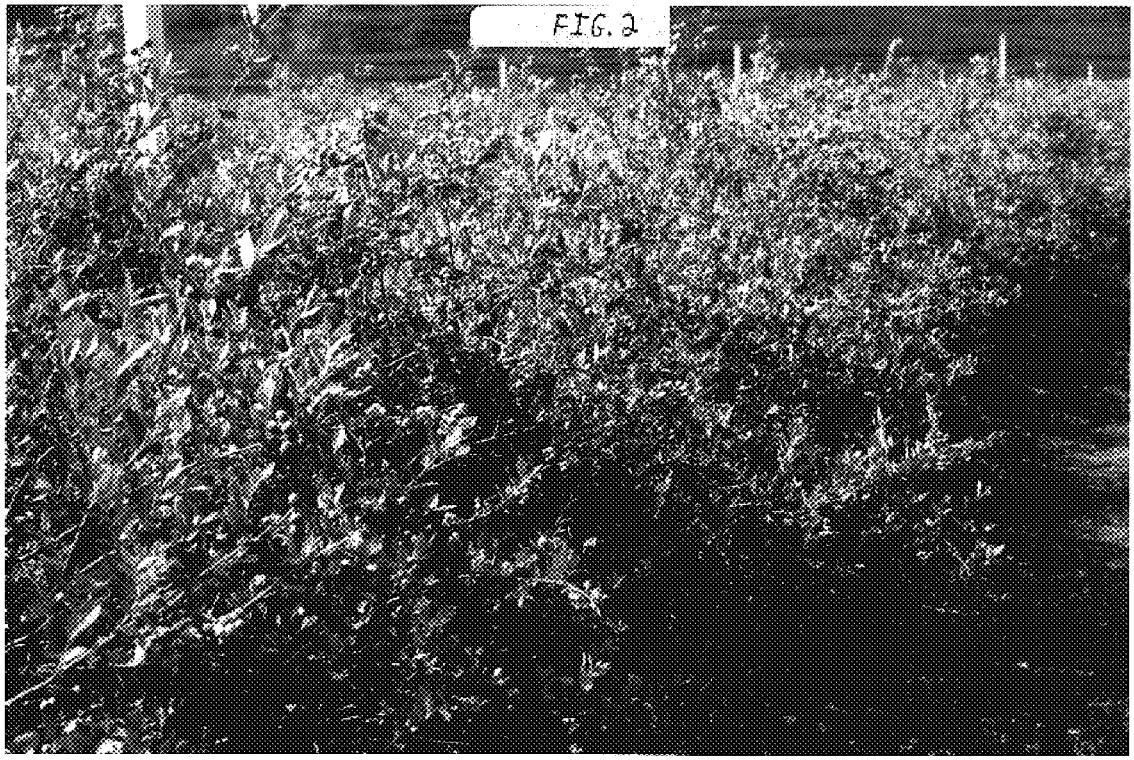
FIG. 2 shows a row of 3-year-old plants including the high vigor and somewhat spreading growth habit of the plants.
Figure 3:
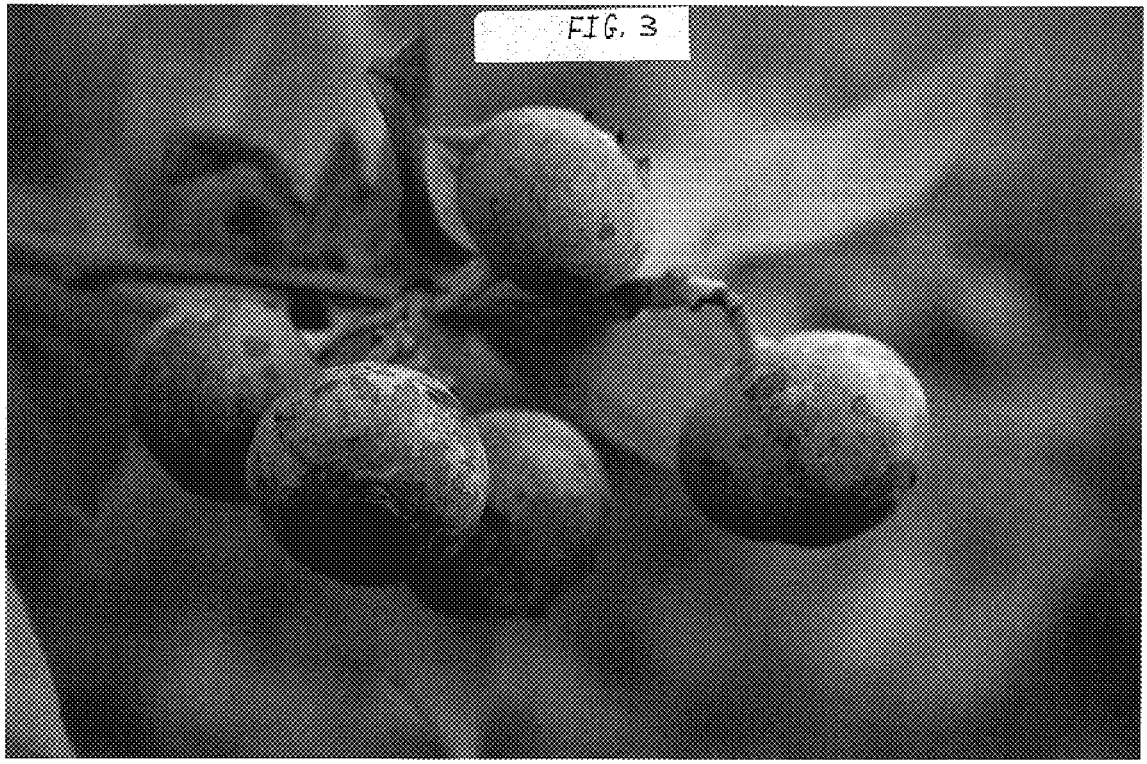
FIG. 3 shows at the close range a cluster of berries ripening in the field. The light-blue color and slight development of the calyx lobes are evident.
Figure 4:
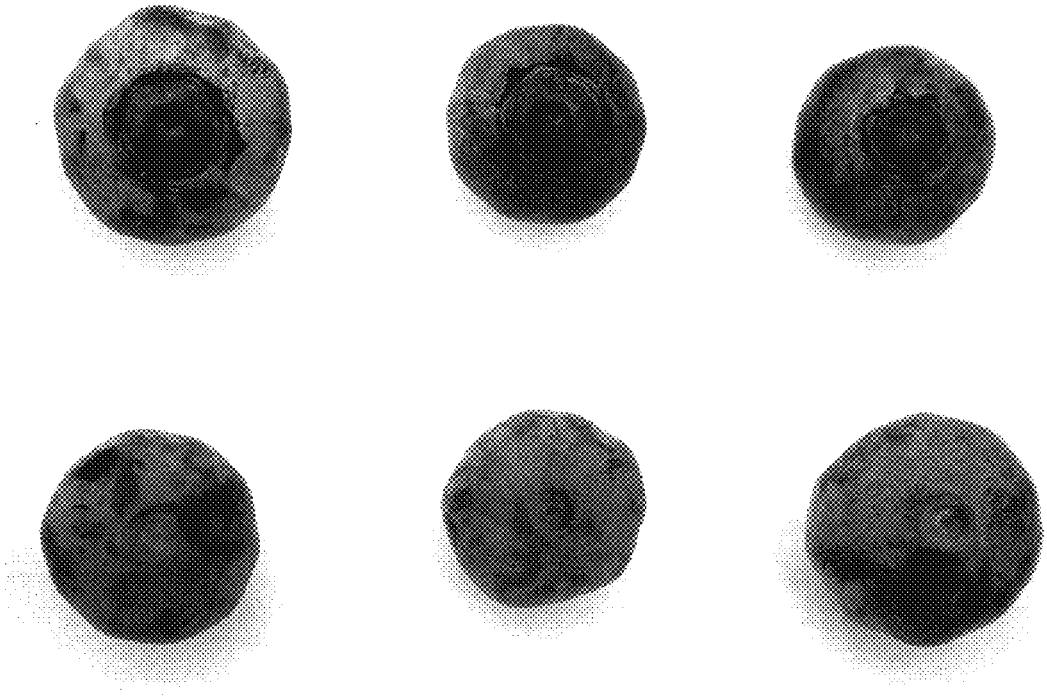
FIG. 4 shows at close range the berries of 'Snowchaser'. Although the picking scars appear somewhat large in these photos, they are dry and the berry has not given problems in shipping.

The following descriptions relate to plants grown in the field in north Florida (Windsor, Fla.). Color designations are from "The Pantone Book of Color" (by Leatrice Eiseman and Lawrence Herbert; Harry N. Abrams, Inc., Publishers, New York, 1990). Where the Pantone color designations differ from the colors in the Drawings, the Pantone colors are the more accurate.

Market class: 'Snowchaser' produces southern highbush blueberries suitable for both in the fresh and processed fruit markets.

Bush: Bush characteristics were observed on a plot of fifty 3-year-old plants growing in a test plot in a commercial field near Windsor in northest Florida.

*Plant height.*—1.5 m.

*Canopy diameter measured at widest part of the bush.*—2.0 m.

*Plant vigor.*—High. More vigorous and faster growing than 'Star'.

*Growth habit.*—Between upright and spreading.

*Flower bud density (number) along flowering twigs in January.*—Medium to high.

*Twigginess.*—Medium.

*Tendency toward evergreenness.*—Medium to high. High tendency to produce some fall flowers.

Trunk and branches:

*Suckering tendency.*—Medium to high. Produces more canes from the base than 'Star'. Plants produce an average of 7 major canes from the ground rising from a crown 45 cm in diameter.

*Surface texture of strong, 1-year-old shoots observed in mid-December.*—Smooth.

*Surface texture of strong, 1-year-old wood observed in December.*—Smooth transitioning to rough.

*Surface texture of 3-year-old and older wood.*—Rough, exfoliating in vertical cracks.

*Color of new twigs observed in mid-December in the field.*—"Willow", Pantone 16-0632 but turning to "Pecan Brown", Pantone 17-1430 in winter on parts exposed to direct sunlight.

*Color of 1-year-old, rough bark observed in mid-December.*—Mottled, changing from "Pecan Brown", Pantone 17-1430 to "Maple Sugar", Pantone 15-1316.

*Color of 3-year-old rough-textured canes.*—"Gray Sand", Pantone 13-1010.

*Internode length on strong, upright shoots measured on Feb. 1.*—1.3 cm.

Leaves:

*Leaf length including petiole, from tip of petiole to end of blade.*—Median 56 mm.

*Leaf width at widest point.*—Medium 29 mm.

*Leaf shape.*—Ovate, terminating in a pronounced dew tip, 0.7 mm long, which is visible with a 15X microscope.

*Leaf margin.*—Minutely serrate with sessile glands along the margin of the petiole half of the leaf blade extending to near the apex on some leaves. These glands are visible at 30X magnification.

*Color of upper surface of leaves.*—"Chive", Pantone 19-0323.

*Color of lower surface of leaves.*—"Sage Green", Pantone 15-0318.

*Pubescense on upper surface of leaves.*—None.

*Pubescence on lower surface of leaves.*—None.

*Pubescence on leaf margins.*—Sessile glands along the margins of the leaf blade extend all the way to the apex of most leaves.

*Relative time of leafing vs flowering.*—Tends to flower before it begins to leaf when coming out of dormancy. Commercially in north and central Florida, plants are often sprayed with formulations of hydrogen cyanomide in midwinter to enhance early leafing.

Flowers:

*Flower arrangement.*—Flowers arranged alternately along a short, leafless, deciduous branch.

*Fragrance.*—Faint smell of Camellia flowers.

*Pedicel length at time of anthesis.*—Median=3 mm.

*Peduncle length at time of anthesis.*—Variable; median=5 mm.

*Flower shape.*—Urceolate.

*Pollen staining with 2% acetocarmine.*—This is a measure of potential pollen fertility. 99%.

*Abundance of pollen shed.*—High.

*Color of dried pollen.*—"Winter White", Pantone 11-0507.

*Flower length, pedicel attachment point to corolla tip excluding the pedicel.*—12 mm.

*Length of corolla tube.*—10 mm.

*Diameter of corolla tube at widest point.*—8 mm.

*Style length.*—Top of ovary to stigma tip. 9 to 10 mm.

*Calyx diameter at anthesis.*—Tip of lobe to tip of opposite lobe. 8 mm.

*Corolla aperture diameter.*—3 mm.

*Calyx surface.*—Smooth.

*Corolla color at anthesis.*—White.

*Corolla surface texture.*—Smooth.

*Calyx color at anthesis.*—"Green Olive", Pantone 17-0535.

*Pistil color at anthesis.*—"Green Banana", Pantone 14-0434.

*Pedicel and peduncle color.*—"Green Olive", Pantone 17-0535.

*Flowering period.*—Mean date of 50% open flower at Windsor, Fla. Feb. 11. Averages 15 days before 'Star'.

*Flower cluster (tight, medium, open).*—Medium to open.

*Number of flowers per cluster.*—Medium=6.

*Location of tip of stigma relative to lip of the corolla.*—Stigma tip extends about 1 mm beyond the end of the corolla tube.

*Self fruitfulness.*—Medium to low. Should be planted with other varieties for cross-pollination.

Berry:

*Mean date of first commercial harvest (25% of the berries ripe).*—April 5.

*Mean date of mid-harvest.*—April 11.

*Mean date of last harvest.*—April 30.

*Diameter of calyx aperture on mature berry.*—6 mm.

*Calyx lobes on mature berry.*—Size and shape. Variable. Calyx lobes typically not well developed but on some berries are developed into a five-pointed star. Calyx dish very shallow and wide. Berry cluster (tight, medium, or loose). Pedicel length on ripe berry 5 mm.

*Peduncle length on ripe berry.*—Variable, typically about 10 mm.

*Number of berries per cluster.*—Median 5.

*Detachment force for ripe berries.*—Medium.

*Mean berry weight on well-pruned plants.*—1.7 g per berry compared to 1.8 for 'Star'.

*Mean berry height.*—13 mm.

*Mean berry width.*—14 to 15 mm.

*Surface color of mature berries while on the plant.*—"Pearl Blue", Pantone 14-4206.

*Surface color of the berries after harvesting and packing.*—"Charcoal Gray", Pantone 18-0601.

*Surface color of ripe berry after polishing.*—"Jet Black", Pantone 19-0303.

*Internal flesh color of ripe berry.*—"Frozen Dew", Pantone 13-0513.

*Berry surface wax.*—Medium amount, medium in persistence during handling of the berry.

*Berry pedicel scar.*—Small and dry.

*Berry firmness.*—High.

*Berry flavor.*—Sweet and low in acidity.

*Berry texture.*—Good: small seeds, very juicy, thin skin.

*Color of dried seeds.*—"Clay", Pantone 15-1231.

*Weight of well-developed dried seeds.*—0.41 mg per seed.

*Length of well-developed, dried seeds.*—Mean=1.9 mm.

*Width of well-developed, dried seeds.*—Mean=1.0 mm.

Physiological characteristics:

*Chilling requirement.*—100–200 hours below 7° C.

*Cold hardiness.*—Flowers and fruit are hardy to −3° C. The plant, during winter dormancy, is hardy to −15° C.

*Productivity.*—In northest Florida, 'Snowchaser' produces about 5 pounds of berries per bush on plants 3 years old or older.

*Ease of propagation.*—'Snowchaser' is easy to propagate from softwood cuttings. The plants survive and grow well in nursery beds. Where hard fall freezes are a possibility, plants of 'Snowchaser' should be hardened in preparation for winter by reducing water and fertilizer in late summer.

Resistance to diseases, insects, and mites: 'Snowchaser' has shown no signs of susceptibility to cane canker (*Botryosphaeria corticis*) in the field. However, stem blight (*Botryosphaeria dothidia*) can be a problem if the plants are stressed by drought, poorly drained soil, or freeze damage. Fungal leaf spots that are common on highbush blueberries grown in Florida are effectively controlled by approved fungicides.

What is claimed is:

1. A new and distinct southern highbush blueberry plant, substantially as illustrated and described, characterized by having a vigorous, spreading bush with a very low chilling requirement that ripens berries extremely early in the spring.

* * * * *